US010441242B2

(12) United States Patent
Kim et al.

(10) Patent No.: US 10,441,242 B2
(45) Date of Patent: Oct. 15, 2019

(54) X-RAY APPARATUS COMPRISING A COLLIMATOR AND METHOD OF OPERATING THE COLLIMATOR

(71) Applicant: SAMSUNG ELECTRONICS CO., LTD., Suwon-si, Gyeonggi-do (KR)

(72) Inventors: Dae-soo Kim, Yongin-si (KR); Han-ju Nam, Anyang-si (KR); Young-jun Lee, Seoul (KR); Jin-ho Choi, Anyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 398 days.

(21) Appl. No.: 14/868,612

(22) Filed: Sep. 29, 2015

(65) Prior Publication Data
US 2016/0220223 A1 Aug. 4, 2016

(30) Foreign Application Priority Data

Feb. 3, 2015 (KR) .................. 10-2015-0016733

(51) Int. Cl.
*A61B 6/00* (2006.01)
*A61B 6/06* (2006.01)
(Continued)

(52) U.S. Cl.
CPC .............. *A61B 6/587* (2013.01); *A61B 6/06* (2013.01); *A61B 6/08* (2013.01); *A61B 6/4085* (2013.01);
(Continued)

(58) Field of Classification Search
CPC ....... A61B 6/06; A61B 6/4085; A61B 6/4208; A61B 6/4233; A61B 6/4283; A61B 6/44;
(Continued)

(56) References Cited

U.S. PATENT DOCUMENTS 6,711,236 B2 * 3/2004 Izuhara .................. A61B 6/035
250/505.1
6,890,099 B2 * 5/2005 Tanaka ..................... A61B 6/08
378/197

(Continued)

FOREIGN PATENT DOCUMENTS

JP 55-88739 7/1980
JP 9-70400 3/1997
(Continued)

OTHER PUBLICATIONS

International Search Report dated Feb. 11, 2016 in corresponding International Patent Application No. PCT/KR2015/011495.
(Continued)

*Primary Examiner* — Allen C. Ho
(74) *Attorney, Agent, or Firm* — Staas & Halsey LLP

(57) ABSTRACT

An X-ray apparatus includes an X-ray source configured to radiate X-rays, a collimator configured to adjust a radiation field of the X-rays and rotate on an optical axis direction of the X-rays, a ring-shaped first rotation transfer unit centered on an optical axis of the X-rays in the X-ray source, a second rotation transfer unit interlocked with the ring-shaped first rotation transfer unit and configured to rotate as the collimator rotates, a rotation sensor configured to sense an amount of rotation of the second rotation transfer unit, and a detector comprising a receiving surface on which the X-rays radiated from the collimator are incident.

11 Claims, 12 Drawing Sheets

(51) Int. Cl.
   *G21K 1/02* (2006.01)
   *G21K 1/04* (2006.01)
   *A61B 6/08* (2006.01)

(52) U.S. Cl.
   CPC .............. *A61B 6/42* (2013.01); *A61B 6/4208* (2013.01); *A61B 6/4233* (2013.01); *A61B 6/4283* (2013.01); *A61B 6/44* (2013.01); *A61B 6/4405* (2013.01); *A61B 6/4452* (2013.01); *A61B 6/4476* (2013.01); *A61B 6/5258* (2013.01); *A61B 6/547* (2013.01); *G21K 1/02* (2013.01); *G21K 1/04* (2013.01); *A61B 6/5205* (2013.01)

(58) Field of Classification Search
   CPC ... A61B 6/4405; A61B 6/4452; A61B 6/4476; A61B 6/547; A61B 6/587; G21K 1/02; G21K 1/04; G21K 1/1046
   USPC .................. 378/150–153, 205, 206
   See application file for complete search history.

(56) References Cited

U.S. PATENT DOCUMENTS

| | | | | |
|---|---|---|---|---|
| 6,893,157 | B2* | 5/2005 | Arakawa | A61B 6/08 378/205 |
| 7,014,362 | B2* | 3/2006 | Beimier | A61B 6/08 378/162 |
| 7,092,489 | B2* | 8/2006 | Li | G21K 1/02 378/147 |
| 7,106,831 | B2* | 9/2006 | Li | G21K 1/02 378/121 |
| 7,123,680 | B2* | 10/2006 | Katada | A61B 6/032 378/16 |
| 7,263,171 | B2* | 8/2007 | Zhang | G21K 1/04 250/505.1 |
| 7,340,032 | B2* | 3/2008 | Besson | A61B 6/025 250/370.1 |
| 7,342,993 | B2* | 3/2008 | Besson | A61B 6/025 250/370.1 |
| 7,343,003 | B2* | 3/2008 | Li | G21K 1/04 250/505.1 |
| 7,382,866 | B2* | 6/2008 | Tan | A61B 6/06 378/147 |
| 7,397,899 | B2* | 7/2008 | Li | G21K 1/02 378/147 |
| 7,401,977 | B2* | 7/2008 | Graumann | A61B 6/4441 378/197 |
| 7,430,280 | B2* | 9/2008 | Song | G21K 1/02 250/497.1 |
| 7,503,692 | B2* | 3/2009 | De Godzinsky | A61B 6/08 378/205 |
| 7,526,065 | B2* | 4/2009 | Hardesty | A61B 6/542 378/145 |
| 7,539,284 | B2* | 5/2009 | Besson | A61B 6/032 378/147 |
| 7,572,057 | B2* | 8/2009 | Takekoshi | A61B 6/4482 378/205 |
| 7,581,885 | B2* | 9/2009 | Ertel | A61B 6/08 378/204 |
| 7,680,249 | B2* | 3/2010 | Yuan | A61B 6/00 378/156 |
| 7,736,055 | B2* | 6/2010 | Hörnig | A61B 6/08 378/206 |
| 7,737,427 | B2* | 6/2010 | Kito | A61B 6/4233 250/370.08 |
| 7,783,007 | B2* | 8/2010 | Echner | A61N 5/1042 378/150 |
| 7,831,023 | B2* | 11/2010 | Wedel | A61B 6/06 378/148 |
| 7,841,772 | B2* | 11/2010 | Nishii | A61B 6/08 378/206 |
| 7,916,835 | B2* | 3/2011 | Abe | A61B 6/06 378/205 |
| 7,949,094 | B2* | 5/2011 | Ahn | A61B 6/447 378/197 |
| 7,970,099 | B2* | 6/2011 | Fadler | G21K 1/046 378/124 |
| 7,997,799 | B2* | 8/2011 | Jabri | A61B 6/4035 378/154 |
| 8,009,794 | B2* | 8/2011 | Partain | A61B 6/032 378/150 |
| 8,009,807 | B2* | 8/2011 | Petrik | G21K 1/04 378/148 |
| 8,019,045 | B2* | 9/2011 | Kato | A61B 6/032 378/116 |
| 8,093,572 | B2* | 1/2012 | Kuduvalli | G21K 1/04 250/492.1 |
| 8,189,743 | B2* | 5/2012 | Yuan | G21K 1/04 378/147 |
| 8,275,187 | B2* | 9/2012 | Oogami | A61B 6/00 378/174 |
| 8,284,903 | B2* | 10/2012 | Yuan | A61B 6/06 378/156 |
| 8,290,119 | B2* | 10/2012 | Tancredi | A61B 6/14 378/197 |
| 8,503,603 | B2* | 8/2013 | Tancredi | A61B 6/0478 378/39 |
| 8,622,614 | B2* | 1/2014 | Carmichael | A61B 6/4266 378/198 |
| 8,670,521 | B2* | 3/2014 | Bothorel | A61B 6/14 378/205 |
| 8,675,820 | B2* | 3/2014 | Baic | A61N 5/00 378/114 |
| 8,678,648 | B2* | 3/2014 | Lalena | A61B 6/4266 378/114 |
| 8,690,426 | B2* | 4/2014 | Liu | G03B 42/02 250/370.09 |
| 8,693,621 | B2* | 4/2014 | Thran | A61B 6/4021 378/17 |
| 8,731,142 | B2* | 5/2014 | Tanabe | G21K 1/046 250/505.1 |
| 8,821,015 | B2* | 9/2014 | Stagnitto | A61B 6/4291 378/205 |
| 8,821,016 | B2* | 9/2014 | Yang | A61B 6/4233 378/205 |
| 8,824,638 | B2* | 9/2014 | Nicholson | A61B 6/06 378/150 |
| 8,827,554 | B2* | 9/2014 | Lalena | A61B 6/46 378/206 |
| 8,942,346 | B2* | 1/2015 | Nicholson | G21K 1/02 378/147 |
| 8,961,011 | B2* | 2/2015 | Lalena | A61B 6/4405 378/197 |
| 8,971,497 | B2* | 3/2015 | Haider | G21K 1/046 378/147 |
| 8,971,498 | B2* | 3/2015 | Haider | G21K 1/04 378/147 |
| 8,976,931 | B2* | 3/2015 | Lalena | A61B 6/4405 378/98.5 |
| 9,014,341 | B2* | 4/2015 | Zhang | A61B 6/03 378/147 |
| 9,036,775 | B2* | 5/2015 | Yoshikawa | A61B 6/145 378/38 |
| 9,036,776 | B2* | 5/2015 | Sadakane | A61B 6/145 378/38 |
| 9,111,656 | B2* | 8/2015 | Schmidt | G21K 1/04 |
| 9,125,572 | B2* | 9/2015 | Noo | A61B 6/027 |
| 9,161,727 | B2* | 10/2015 | Jenkins | G21K 1/04 |
| 9,198,626 | B2* | 12/2015 | Heuscher | A61B 6/032 |
| 9,259,191 | B2* | 2/2016 | Noo | G21K 1/02 |
| 9,348,055 | B2* | 5/2016 | Abenaim | G01V 5/0008 |
| 9,357,971 | B2* | 6/2016 | Yoshikawa | A61B 6/032 |
| 9,406,411 | B2* | 8/2016 | Sayeh | G21K 1/04 |
| 9,451,923 | B2* | 9/2016 | Hemmendorff | A61B 6/4452 |
| 9,462,985 | B2* | 10/2016 | Hu | A61B 6/547 |
| 9,521,983 | B2* | 12/2016 | Jang | A61B 6/4429 |
| 9,566,040 | B2* | 2/2017 | Hu | A61B 6/5205 |

(56) References Cited

U.S. PATENT DOCUMENTS

| | | | |
|---|---|---|---|
| 9,572,544 B2* | 2/2017 | O'Dea | A61B 6/547 |
| 9,592,014 B2* | 3/2017 | Melman | A61B 6/06 |
| 9,597,040 B2* | 3/2017 | Hemmendorff | A61B 6/025 |
| 9,730,656 B2* | 8/2017 | Hyde | A61B 6/145 |
| 9,820,709 B2* | 11/2017 | Melman | G21K 1/04 |
| 9,892,810 B2* | 2/2018 | Kwerreveld | G21K 1/046 |
| 9,931,087 B2* | 4/2018 | Melman | G21K 1/04 |
| 10,149,654 B2* | 12/2018 | Melman | A61B 6/06 |
| 2005/0069088 A1 | 3/2005 | Li | |
| 2007/0183578 A1 | 8/2007 | Song | |
| 2008/0118023 A1 | 5/2008 | Besson | |
| 2013/0058462 A1 | 3/2013 | Jenkins et al. | |
| 2014/0126694 A1 | 5/2014 | Abenaim et al. | |
| 2014/0198896 A1 | 7/2014 | Hemmendorff et al. | |

FOREIGN PATENT DOCUMENTS

| | | |
|---|---|---|
| JP | 2001-258871 | 9/2001 |
| JP | 2005/000372 | 1/2005 |
| JP | 2005-106799 | 4/2005 |
| JP | 2005-329033 | 12/2005 |
| JP | 2012-170618 | 9/2012 |
| WO | 2014/078808 A2 | 5/2014 |

OTHER PUBLICATIONS

Partial Supplementary European Search Report dated Jan. 23, 2018 in corresponding European Patent Application No. 15881304.8, 13 pages.
Supplementary European Search Report issued in Application No. 15881304.8 dated May 30, 2018 (11 pages).

* cited by examiner

X-RAY APPARATUS COMPRISING A COLLIMATOR AND METHOD OF OPERATING THE COLLIMATOR

CROSS-REFERENCE TO RELATED APPLICATION

This application claims the benefit of Korean Patent Application No. 10-2015-0016733, filed on Feb. 3, 2015, in the Korean Intellectual Property Office, the disclosure of which is incorporated herein in its entirety by reference.

BACKGROUND

1. Field

One or more exemplary embodiments relate to an x-ray apparatus and a method of operating the same.

2. Description of the Related Art

In general, X-rays are electromagnetic waves that have a wavelength of 0.01 to 100 ☐ and can pass through an object. Thus, they may be commonly used in a wide range of applications, such as medical equipment for taking images of inner parts of a living body and non-destructive testing equipment for industrial use.

According to its basic operating principle, an X-ray apparatus includes an X-ray source that emits X-rays. The X-rays pass through an object and a difference between the intensities of the X-rays that passed through the object is detected by using an X-ray detector to thereby identify the internal structure of the object and diagnose the object. As the transmission coefficient of X-rays varies with the density of the object and the atomic number of atoms of the object, it is possible to easily identify the internal structure of the object via the X-ray apparatus.

However, X-rays are radioactive rays, and thus, when an object is exposed to X-rays for a long time, tissues of the object may be damaged and various diseases may be caused. To prevent such unfavorable side effects, an X-ray apparatus includes an X-ray radiation range control system to adjust a radiation range of X-rays irradiated toward an object.

For example, a medical X-ray apparatus may include a collimator to adjust a radiation range of the X-rays in a range defined by a top-bottom direction and a left-right direction. In this case, the radiation range may be limited to a specific region by manually or automatically controlling a radiation range of the collimator. Accordingly, an examination region of an object and a radiation range of the X-rays have to be aligned since the radiation range of the X-rays may be limited to a specific region.

SUMMARY

One or more exemplary embodiments include an X-ray apparatus whereby alignment between an X-ray radiator and a detector may be controlled.

One or more exemplary embodiments include a method of operating the X-ray apparatus.

Additional aspects will be set forth in part in the description which follows and, in part, will be apparent from the description, or may be learned by practice of the presented exemplary embodiments.

According to one or more exemplary embodiments, an X-ray apparatus includes an X-ray source configured to radiate X-rays, a collimator configured to adjust a radiation field of the X-rays and rotate about an optical axis direction of the X-rays, a ring-shaped first rotation transfer unit centered on an optical axis of the X-rays in the X-ray source, a second rotation transfer unit configured to rotate as the collimator rotates while being interlocking with the ring-shaped first rotation transfer unit, a rotation sensor configured to sense an amount of rotation of the second rotation transfer unit, and a detector comprising a receiving surface on which the X-rays radiated from the collimator are incident.

The X-ray apparatus may further include a connector configured to connect the X-ray source to the collimator, wherein the connector has a ring shape with open ends, an end of the connector being fixedly connected to the X-ray source and other end of the connector being rotatably connected to the collimator.

The first rotation transfer unit may be placed along an outer circumferential surface of the connector, and the second rotation transfer unit and the rotation sensor are placed outside the connector.

The first rotation transfer unit may be placed along an inner circumferential surface of the connector, and the second rotation transfer unit and the rotation sensor are placed inside the connector.

The first rotation transfer unit and the second rotation transfer unit may comprise a pair of gear units together, and the pair of gear units may rotate while interlocking with each other.

The first rotation transfer unit and the second rotation transfer unit may commonly comprise a pair of roller units that may rotate according to a sliding motion while being in contact with each other.

The rotation sensor may be a position meter or an encoder.

The X-ray apparatus may further include a driving motor configured to rotate the collimator about the optical axis direction of the X-rays, and a controller configured to receive the amount of rotation of the collimator from the rotation sensor and transmit a driving signal to the driving motor according to the received amount of rotation of the collimator.

The X-ray apparatus may further include a driving motor configured to rotate the detector about the optical axis direction of the X-rays, and a controller configured to receive the amount of rotation of the collimator from the rotation sensor and transmit a driving signal to the driving motor according to the amount of rotation of the collimator.

The collimator may include an X-ray entrance window through which the X-rays enter and an X-ray exit window through which the X-rays exit, and the X-ray apparatus may further include one or more radiation field range adjustors placed in the X-ray entrance window and the X-ray exit window.

The X-ray apparatus may further include an image generator configured to generate an image signal based on a detection signal generated by the X-rays incident on the receiving surface of the detector, and an output unit configured to output an image based on the image signal generated by the image generator, wherein the image generator is further configured to receive the amount of rotation of the collimator from the rotation sensor and determine the amount of rotation of the image generated based on the image signal.

According to one or more exemplary embodiments, a method of operating an X-ray apparatus includes obtaining information about a position of a detector comprising a receiving surface on which X-rays radiated from an X-ray source are incident, sensing, via a rotation sensor, an amount of rotation of a collimator rotating on an optical axis direction of the X-rays, and aligning a radiation field of X-rays with the receiving surface of the detector based on the amount of rotation of the collimator and the information about the position of the detector.

The radiation field of X-rays and the receiving surface of the detector may be aligned with each other by rotating the collimator about the optical axis direction of the X-rays via a driving motor that rotates the collimator about the optical axis direction of the X-rays.

The radiation field of X-rays and the receiving surface of the detector may be aligned with each other by rotating the detector rotate about the optical axis direction of the X-rays via a driving motor that rotates the detector about the optical axis direction of the X-rays.

The radiation field of X-rays and the receiving surface of the detector may be aligned with each other by rotating the collimator and the detector rotate about the optical axis direction of the X-rays via a first driving motor configured to drive the collimator and a second driving motor configured to drive the detector, respectively.

According to one or more exemplary embodiments, a method of operating an X-ray apparatus includes obtaining information about a position of a detector comprising a receiving surface on which X-rays radiated from an X-ray source are incident, sensing via a rotation sensor, a rotation extent of a collimator rotating about an optical axis direction of the X-rays, determining an amount of rotation of a detection signal generated by the X-rays incident on the receiving surface of the detector, based on the amount of rotation of the collimator and the information about the position of the detector, generating a corrected image signal based on the amount of rotation of the detection signal, and outputting an image to an output unit based on to the corrected image signal.

According to one or more exemplary embodiments, there is provided a non-transitory computer-readable recording medium having recorded thereon a program for executing one of the methods above.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
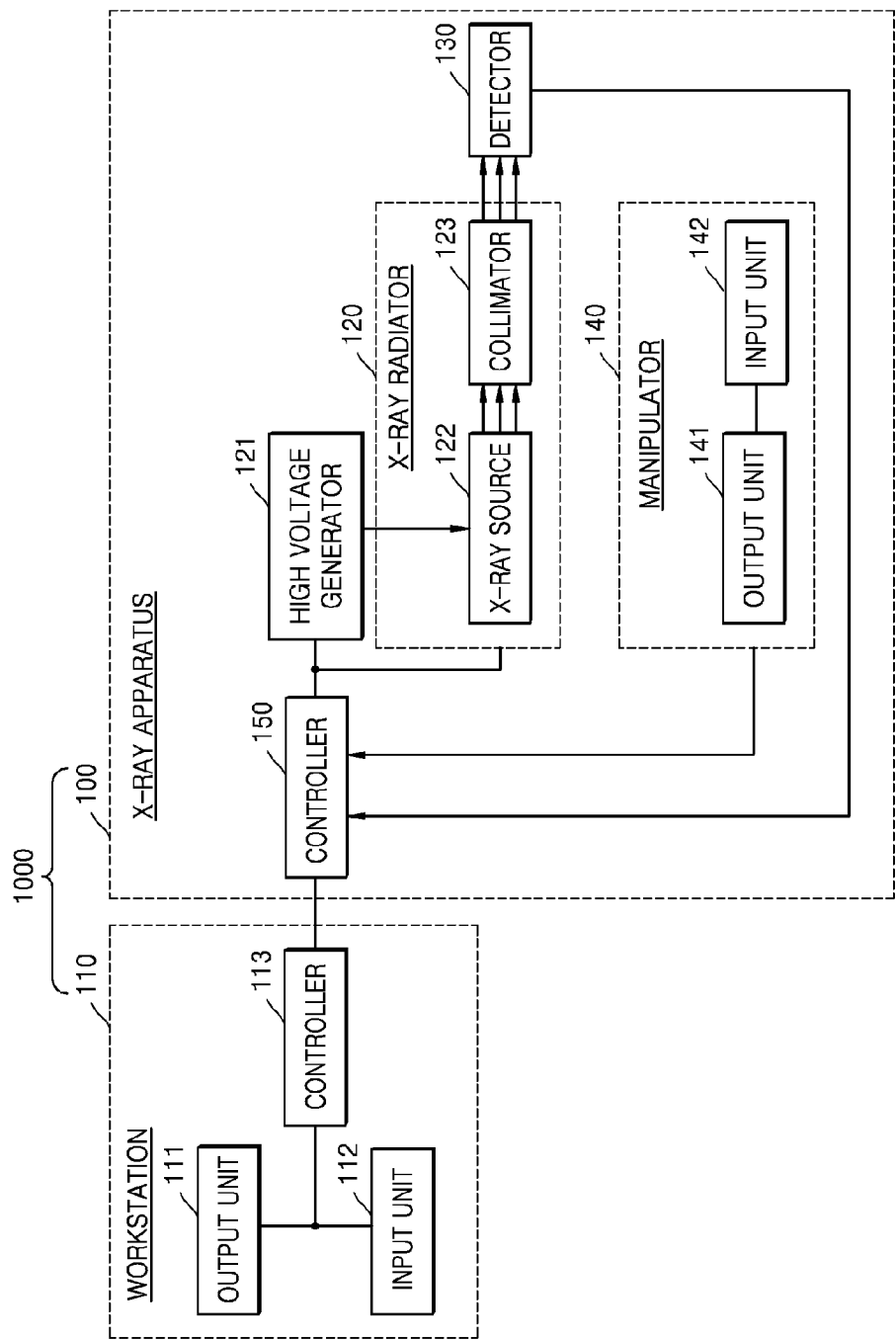
FIG. 1 is a block diagram of an X-ray system according to an exemplary embodiment.

The attached drawings for illustrating exemplary embodiments of the present disclosure are referred to in order to gain a sufficient understanding of the present disclosure, the merits thereof, and the objectives accomplished by the implementation of the present disclosure. The embodiment concept may, however, be embodied in many different forms and should not be construed as being limited to the embodiments set forth herein; rather, these embodiments are provided such that this disclosure will be thorough and complete, and will fully convey the embodiment concept to one of ordinary skill in the art.

Hereinafter, the terms used in the specification will be briefly described, and then the present disclosure will be described in detail.

The terms used in this specification are those general terms currently widely used in the art in consideration of functions regarding the present disclosure, but the terms may vary according to the intention of those of ordinary skill in the art, precedents, or new technology in the art. Also, specified terms may be selected by the applicant, and in this case, the detailed meaning thereof will be described in the detailed description of the embodiments. Thus, the terms used in the specification should be understood not as simple names but based on the meaning of the terms and the overall description of the embodiments.

Throughout the specification, an "image" may denote multi-dimensional data including discrete image elements (for example, pixels in a two-dimensional image or voxels in a three-dimensional image). For example, an image may be a medical image of an object acquired by an X-ray apparatus, a computed tomography (CT) apparatus, a magnetic resonance imaging (MRI) apparatus, an ultrasound diagnosis apparatus, or another medical imaging apparatus.

In addition, an "object" may be a human, an animal, or a part of a human or animal. For example, the object may include an organ (for example, the liver, the heart, the womb, the brain, breasts, or the abdomen), blood vessels, or a combination thereof. The object may be a phantom. The phantom denotes a material having a volume, a density, and an effective atomic number that are approximately the same as those of a living organism. For example, the phantom may be a spherical phantom having similar properties to the human body.

Throughout the specification, a "user" may be, but is not limited to, a medical expert, for example, a medical doctor, a nurse, a medical laboratory technologist, or a medical imaging expert, or a technician who repairs medical apparatuses.

An X-ray apparatus is a medical imaging apparatus that acquires images of internal structures of an object by transmitting X-rays through the human body. The X-ray apparatus may acquire medical images of an object more simply and within a shorter time than other medical imaging apparatuses including an MRI apparatus and a CT apparatus. Therefore, the X-ray apparatus is widely used for simple chest photographing, simple abdomen photographing, simple skeleton photographing, simple nasal sinuses photographing, simple neck soft tissue photographing, and breast photographing.

Figure 2:
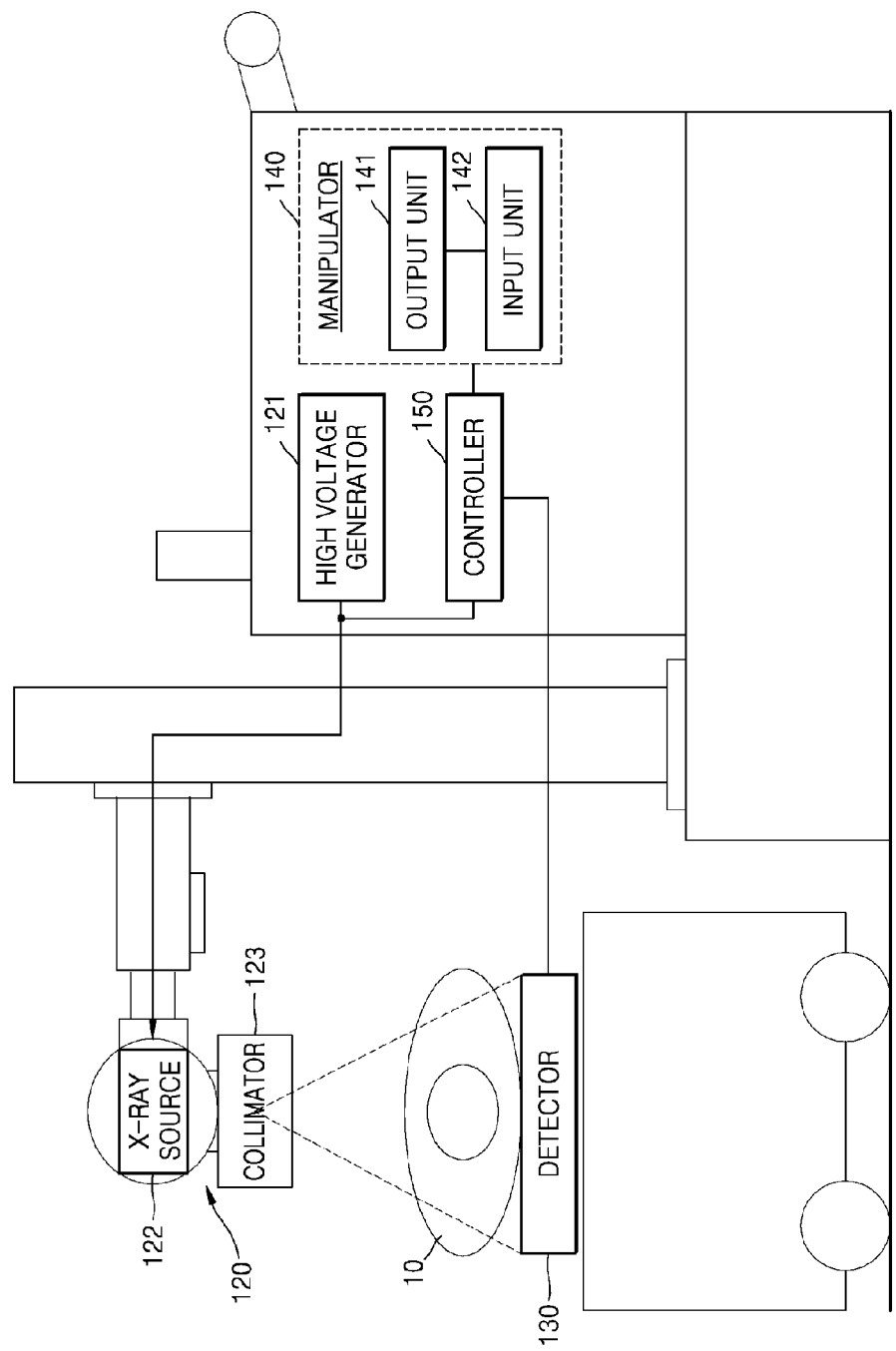
FIG. 2 is a schematic diagram illustrating an example of diagnosing an object by using the X-ray system of FIG. 1, according to an exemplary embodiment.

FIG. 1 is a block diagram of an X-ray system 1000 according to an exemplary embodiment. FIG. 2 is a schematic diagram illustrating an example of diagnosing an object 10 by using the X-ray system 1000, according to an exemplary embodiment.

Referring to FIGS. 1 and 2, the X-ray system 1000 may include an X-ray apparatus 100 and a workstation 110. The X-ray apparatus 100 may be a fixed-type X-ray apparatus or a mobile X-ray apparatus. The X-ray apparatus 100 may include an X-ray radiator 120, a high voltage generator 121, a detector 130, a manipulator 140, and a controller 150. The controller 150 may control overall operations of the X-ray apparatus 100.

The high voltage generator 121 may generate a high voltage for generating X-rays and send the high voltage to an X-ray source 122.

The X-ray radiator 120 may include the X-ray source 122 that receives the high voltage from the high voltage generator 121 to generate and radiate X-rays, and a collimator 123 configured to guide a path of the X-rays radiated from the X-ray source 122 and adjust an irradiation region radiated by the X-rays.

The X-ray source 122 may include an X-ray tube, for example, a vacuum tube diode including a cathode and an anode. The X-ray source 122 is configured to generate a high vacuum of about 10 mmHg in the X-ray tube and heat a filament of the anode at a high temperature to generate thermal electrons. For example, the filament may be a tungsten filament, and a voltage of about 10V and a current of about 3 to 5 A may be applied to an electric wire connected to the filament to heat the filament. In this case, when a high voltage of about 10 to about 300 kVp is applied between the cathode and the anode, the thermal electrons may be accelerated and thus collide with a target material of the cathode, thereby X-rays being generated. The X-rays are radiated outside via a window that may include a beryllium thin film. When a high voltage is applied between the cathode and the anode, most of the energy of the thermal electrons that collide with the target material is consumed as heat and the remaining energy is converted into X-rays.

The voltage applied between the cathode and the anode of the X-ray tube is referred to as a tube voltage, and the tube voltage is applied from the high voltage generator 121 and a magnitude of the tube voltage may be expressed by a crest value (kVp). When the tube voltage increases, a velocity of the thermal electrons increases, and accordingly, energy of the X-rays (energy of photons) that are generated when the thermal electrons collide with the target material is increased. The current flowing in the X-ray tube is referred to as a tube current that may be expressed as an average value (mA). When the tube current increases, the number of thermal electrons emitted from the filament is increased, and accordingly, the X-ray dose (the number of X-ray photons) generated when the thermal electrons collide with the target material is increased. Therefore, the energy of the X-rays may be adjusted according to the tube voltage, and the intensity of the X-rays or the X-ray dose may be adjusted according to the tube current and the X-ray exposure time.

The detector 130 detects X-rays that are radiated from the X-ray radiator 120 and have passed through an object. The detector 130 may be a digital detector. The detector 130 may include a receiving surface 131 (refer to FIG. 4A) on which X-rays radiated from the X-ray source 122 may be incident. The receiving surface 131 may include a thin film transistor (TFT) or a charge coupled device (CCD). The detector 130 may be a fixed-type detector or a rotation-type detector that may move linearly to a predetermined position or rotate as illustrated in FIG. 2.

The X-ray apparatus 100 may further include a manipulator 140 configured to provide a user with an interface for manipulating the X-ray apparatus 100. The manipulator 140 may include an output unit 141 and an input unit 142. The input unit 142 may receive from a user a command for manipulating the X-ray apparatus 100 and various types of information related to X-ray photographing. The controller 150 may control or manipulate the X-ray apparatus 100 according to the information received by the input unit 142. The output unit 141 may output information related to a photographing operation such as the X-ray radiation under the control of the controller 150.

The workstation 110 and the X-ray apparatus 100 may be connected to each other by wire or wirelessly. When the workstation 110 and the X-ray apparatus 100 are connected to each other wirelessly, a device (not shown) for synchronizing clock signals with each other may be further included in the X-ray apparatus 100. The workstation 110 and the X-ray apparatus 100 may be placed within physically separate spaces.

The workstation 110 may include an output unit 111, an input unit 112, and a controller 113. The output unit 111 and the input unit 112 provide a user with an interface for manipulating the workstation 110 and the X-ray apparatus 100. The controller 113 may control the workstation 110 and the X-ray apparatus 100.

The X-ray apparatus 100 may be controlled via the workstation 110 or may be controlled via the controller 150 included in the X-ray apparatus 100. Accordingly, a user may control the X-ray apparatus 100 via the workstation 110 or may control the X-ray apparatus 100 via the manipulator 140 and the controller 150 included in the X-ray apparatus 100. In other words, a user may remotely control the X-ray apparatus 100 via the workstation 110 or may directly control the X-ray apparatus 100.

Although the controller 113 of the workstation 110 is separate from the controller 150 of the X-ray apparatus 100 in FIG. 1, the embodiment concept is not limited thereto. For example, the controllers 113 and 150 may be integrated into a single controller, and the single controller may be included only in one of the workstation 110 and the X-ray apparatus 100. Hereinafter, the controllers 113 and 150 may denote the controller 113 of the workstation 110 and/or the controller 150 of the X-ray apparatus 100.

The output unit 111 and the input unit 112 of the workstation 110 may provide a user with an interface for manipulating the X-ray apparatus 100, and the output unit 141 and the input unit 142 of the X-ray apparatus 100 may also provide a user with an interface for manipulating the X-ray apparatus 100. Although the workstation 110 and the X-ray apparatus 100 include the output units 111 and 141, respectively, and the input units 112 and 142, respectively, in FIG. 1, embodiments are not limited thereto. Only one selected from the workstation 110 and the X-ray apparatus 100 may include an output unit or an input unit.

Hereinafter, the input units 112 and 142 may denote the input unit 112 of the workstation 110 and/or the input unit 142 of the X-ray apparatus 100, and the output units 111 and 141 may denote the output unit 111 of the workstation 110 and/or the output unit 141 of the X-ray apparatus 100.

Examples of the input units 112 and 142 may include a keyboard, a mouse, a touch screen, a voice recognizer, a fingerprint recognizer, an iris recognizer, and other input devices which are well known to one of ordinary skill in the art. The user may input a command for radiating the X-rays via the input units 112 and 142, and the input units 112 and 142 may include a switch for inputting the command.

The controllers 113 and 150 control positions of the X-ray radiator 120 and the detector 130, photographing timing, and photographing conditions, according to photographing conditions set by the user.

In more detail, the controllers 113 and 150 may control the X-ray source 122 and the detector 130 according to the command input via the input units 112 and 142 so as to control radiation timing of the X-rays, an intensity of the X-rays, and a region radiated by the X-rays. In addition, the control units 113 and 150 may adjust the position of the detector 130 according to a predetermined photographing condition and control operation timing of the detector 130. Furthermore, the controllers 113 and 150 may generate a medical image of the object 10 based on image data received via the detector 130. In detail, the controllers 113 and 150 may receive the image data from the detector 130, and then, generate the medical image of the object by removing noise from the image data and adjusting a dynamic range and interleaving of the image data. The alignment between the X-ray source 122 and the detector 130, which is controlled by the controllers 113 and 150, and the generation of a medical image of the object 10 will be described in detail later.

The output units 111 and 141 may output the medical image generated by the controllers 113 and 150. The output units 111 and 141 may output information that is necessary for the user to manipulate the X-ray apparatus 100, for example, a user interface (UI), user information, or object information. Examples of the output units 111 and 141 may include a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a three-dimensional (3D) display, a transparent display, and other various output devices well known to one of ordinary skill in the art.

Figure 3A:
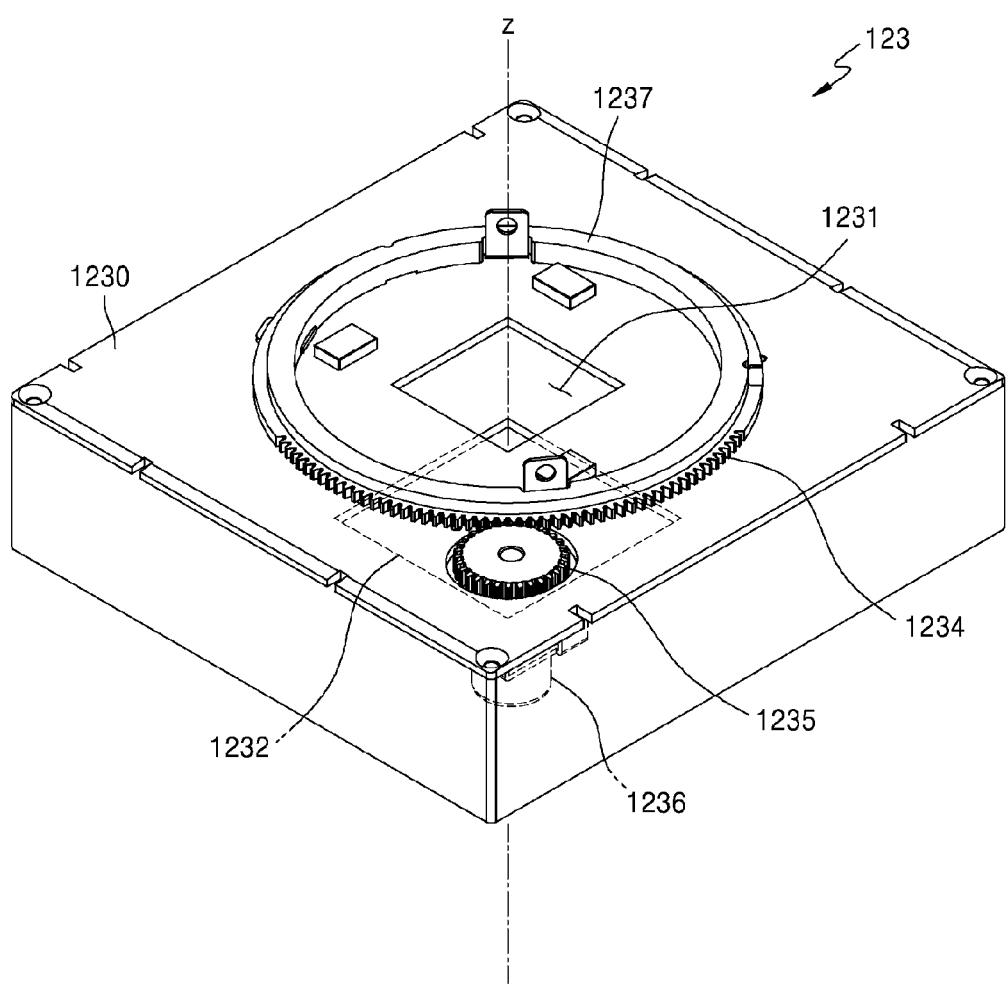
FIG. 3A is a perspective view of a collimator including a connector according to an exemplary embodiment.
Figure 3B:
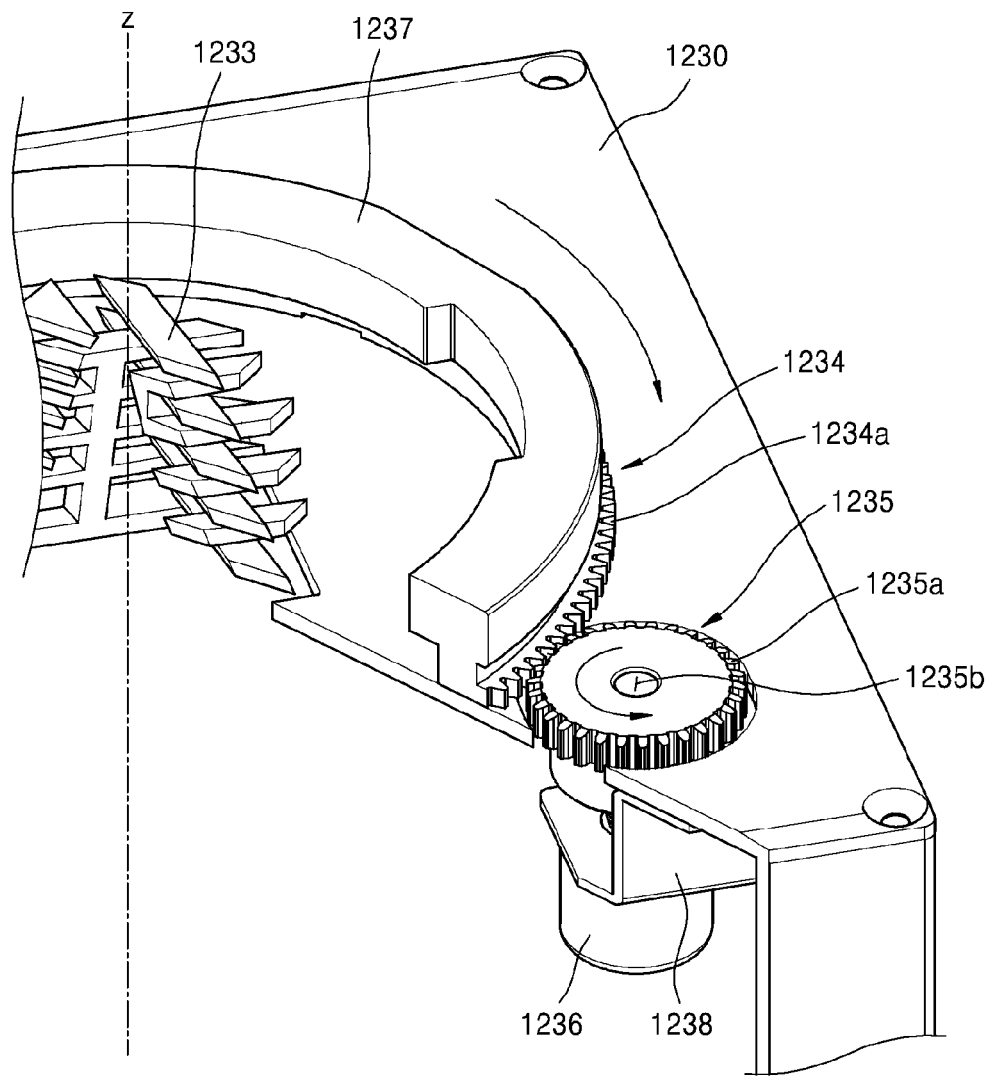
FIG. 3B is a sectional perspective view of a collimator including a connector according to an exemplary embodiment.
Figure 4A:
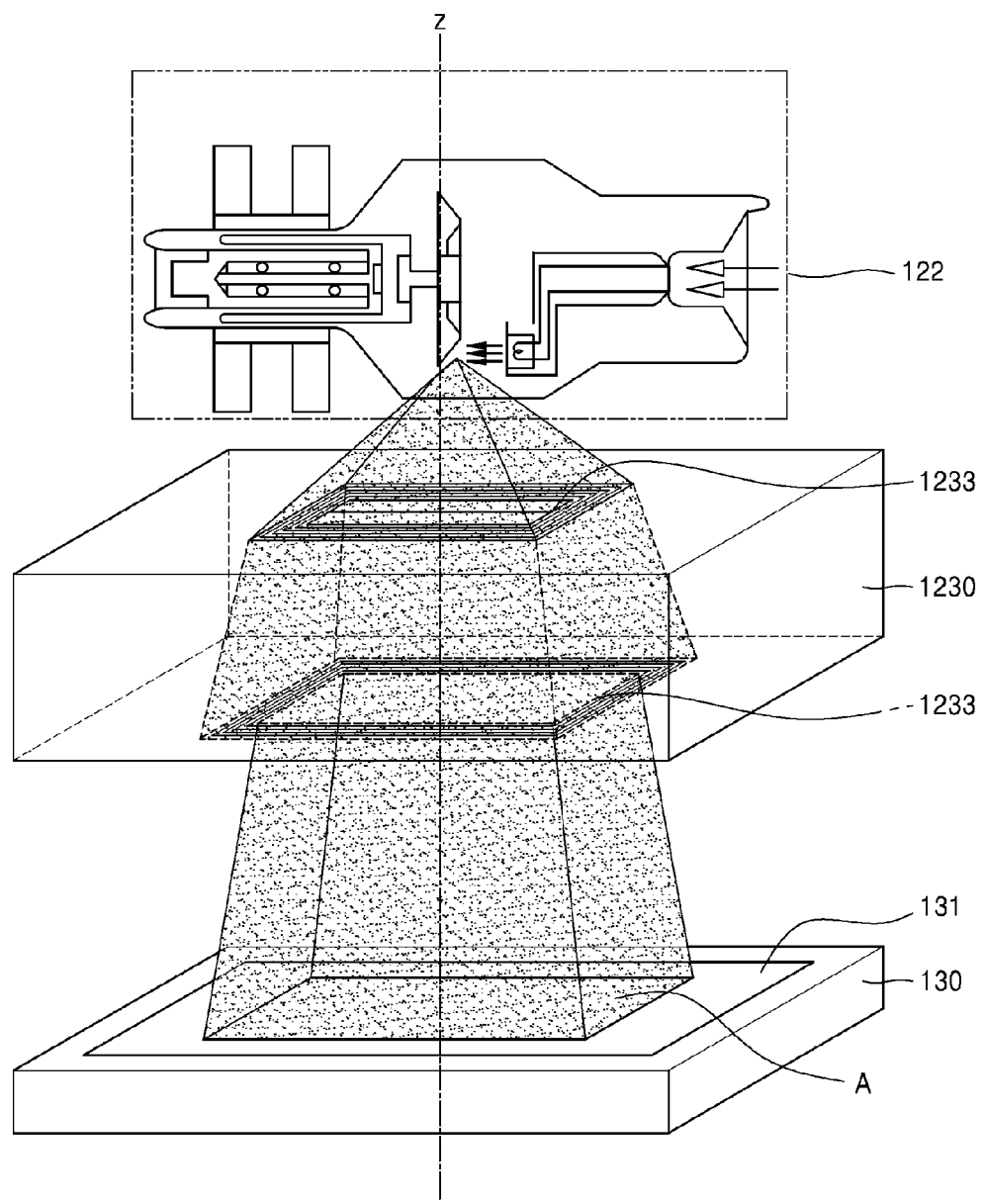
FIGS. 4A and 4B are schematic diagrams of an X-ray radiator and a detector according to an exemplary embodiment.
Figure 4B:
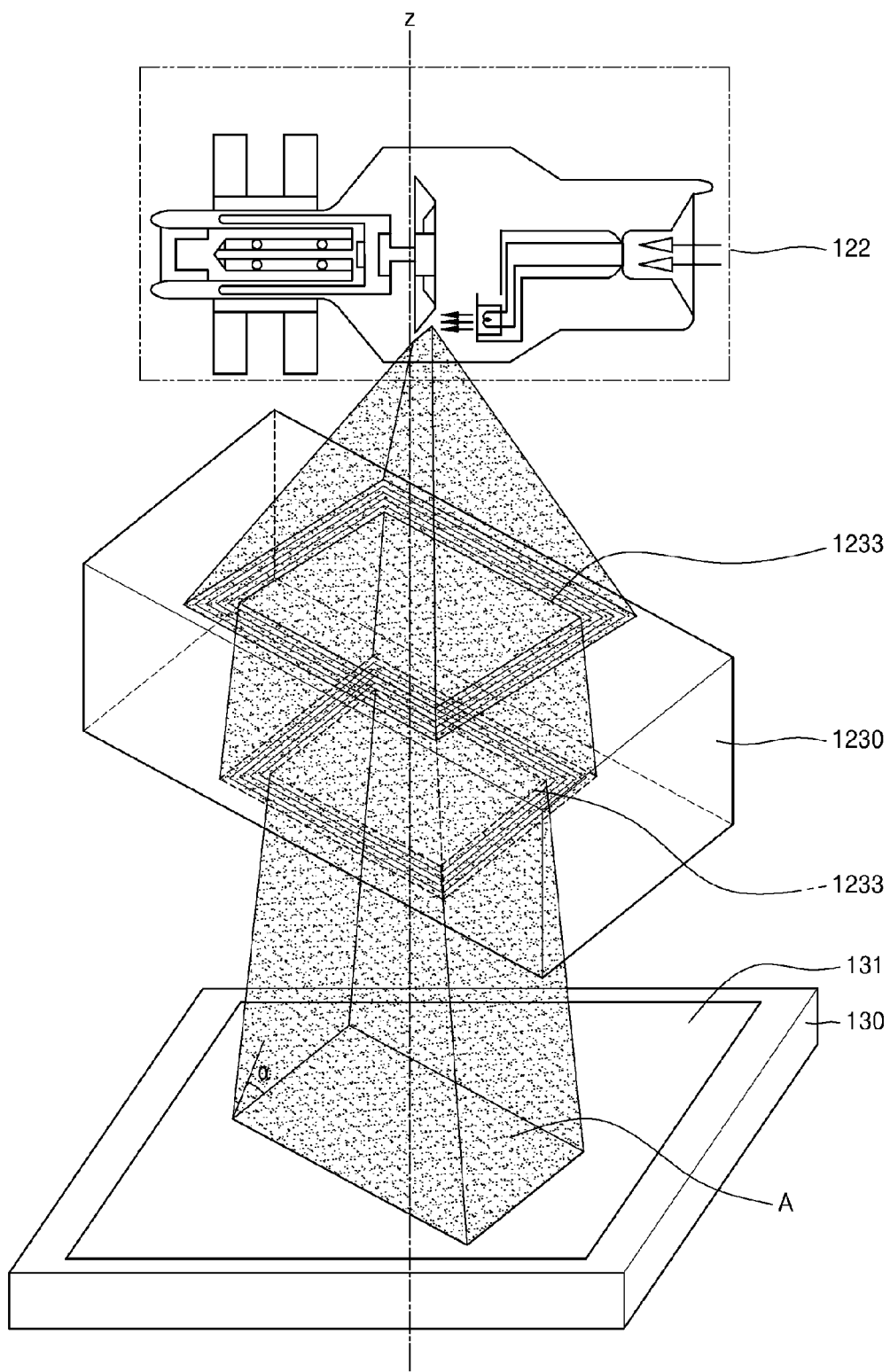

FIG. 3A is a perspective view of a collimator 123 including a connector 1237 according to an exemplary embodiment. FIG. 3B is a sectional perspective view of a collimator 123 including a connector 1237 according to an exemplary embodiment. FIGS. 4A and 4B are schematic diagrams of an X-ray radiator 120 and a detector 130 according to an exemplary embodiment. Component elements that are the same as those of FIGS. 1 and 2 from among component elements included in an X-ray radiator 120 illustrated in FIGS. 3A, 3B, 4A, and 4B use the same reference numerals as FIGS. 1 and 2, and repeated descriptions are omitted.

Referring to FIGS. 3A and 3B, the collimator 123 may include a collimator box 1230, an entrance window 1231 at which X-rays radiated from the X-ray source 122 enters, an exit window 1232 through which the X-rays entering from the X-ray source 122 exits toward an object 10, and at least one radiation field range adjustor 1233 that may be disposed in the entrance window 1231 and the exit window 1232.

The collimator box 1230 is a shielding member for limiting the direction and diffusion of the X-rays radiated from the X-ray source 122. The collimator box 1230 may prevent radioactive rays other than X-rays to be used in diagnosis from being radiated to the outside. The collimator box 1230 may be formed of tungsten or lead which is capable of absorbing radioactive rays. However, the embodiment concept is not limited thereto. For example, the material of the collimator box 1230 and the thickness and size of the collimator box 1230 may be differently determined according to the amount of energy of radioactive rays that are radiated from the X-ray source 122. The collimator box 1230 may include an X-ray passing path connected from the entrance window 1231 up to the exit window 1232 so that X-rays entering from the X-ray source 122 may exit toward the object 10.

The entrance window 1231 is a window prepared so that X-rays radiated from the X-ray source 122 may enter the collimator 123. The entrance window 1231 is formed in one side of the collimator box 1230 and is disposed to face the X-ray source 122.

The exit window 1232 is a window prepared so that X-rays input through the entrance window 1231 may exit toward the object 10 after passing through collimator box 1230. The exit window 1232 may be formed in another side of the collimator box 1230, which faces one side of the collimator box 1230 in which the entrance window 1231 is formed.

The at least one radiation field range adjustor 1233 is a blocking member that may adjust a radiation field of X-rays. For example, the radiation field range adjustor 1233 may have an aperture form having a rectangular-type opening shape. A radiation range of X-rays radiated to the object 10 and the detector 130 may be determined depending on an extent of opening and closing of the radiation field range adjustor 1233, for example, an extent of opening or closing of an aperture the radiation field range adjustor 1233. The at least one radiation field range adjustor 1233 may be disposed in any one selected from the entrance window 1231 and the exit window 1232 or may be disposed in both the entrance window 1231 and the exit window 1232.

A connector 1237 may be disposed between the X-ray source 122 and the collimator box 1230 to connect the X-ray source 122 to collimator box 1230. For example, the connector 1237 may be formed in a ring shape having a hollow, which extends in a radiation direction of X-rays. One end of the connector 1237 may be rotatably connected to the entrance window 1231 and the other end of the connector 1237 may be fixedly connected to the X-ray source 122, and thus, X-rays radiated from the X-ray source 122 may pass through the collimator 123. For example, one end of the connector 1237 may be rotatably connected to the collimator box 1230 to rotate on an optical axis direction Z of X-rays, and the other end of the connector 1237 may be fixedly connected to the X-ray source 122.

Referring to FIGS. 2, 4A, and 4B, when the object 10 is diagnosed by using the X-ray system 1000, a user may adjust an irradiation area of the object 10 by adjusting the opening and closing of the radiation field range adjustor 1233 or radiating the collimator 123. For example, when collimator 123 includes the collimator box 1230 and the at least one radiation field range adjustor 1233, X-rays passing through the collimator 123 may be incident on the receiving surface 131 of the detector 130.

An area of the receiving surface 131 on which the X-rays are incident after passing through the collimator 123 is referred to as a radiation field A of X-rays. The radiation field A of X-rays may be determined depending on the extent of opening and closing of the aperture disposed in the radiation field range adjustor 1233 and the rotation of the collimator 123. Accordingly, an irradiation area of the object 10 may be accurately adjusted by controlling the radiation field A of X-rays depending on the extent of opening and closing of the aperture disposed in the radiation field range adjustor 1233 and the rotation of the collimator 123. In this case, the collimator 123 rotates on the optical axis direction Z of X-rays to control the radiation field A of X-rays, whereas the position of the detector 130 is fixed. Thus, misalignment by a predetermined angle, for example, a first angle α, may occur between the radiation field A of X-rays and the receiving surface 131 of the detector 130. Accordingly, if the amount of rotation of the collimator 123 rotating on the optical axis direction Z of X-rays may be sensed, the misalignment between the radiation field A of X-rays and the receiving surface 131 of the detector 130 may be adjusted.

Referring back to FIGS. 3A and 3B, the X-ray radiator 120 may include a first rotation transfer unit 1234 disposed to be fixed to the X-ray source 122, a second rotation transfer unit 1235 that may rotate while interlocking with the first rotation transfer unit 1234, and a rotation sensor 1236 that may receive a rotation from the second rotation transfer unit 1235 and sense the rotation of the collimator 123.

The first rotation transfer unit 1234 may be disposed to be fixed to the X-ray source 122 and rotate while interlocking with the second rotation transfer unit 1235. For example, the first rotation transfer unit 1234 may be formed in a ring shape having a hollow and be disposed to be fixed to an outer circumferential portion of the connector 1237 having a ring shape. A plurality of first gear units 1234*a* may be disposed on an outer circumferential surface of the first rotation transfer unit 1234.

The second rotation transfer unit 1235 may be disposed in the rotation sensor 1236 to be described later and transfer the rotation of the collimator 123 to the rotation sensor 1236. For example, the second rotation transfer unit 1235 may be formed in the shape of a disk and transfer the amount of rotation of the collimator 123, which rotates on the optical axis direction Z of X-rays by rotating while interlocking with the first rotation transfer unit 1234, to the rotation sensor 1236. For example, a plurality of second gear units 1235*a* may be disposed along an outer circumferential surface of the second rotation transfer unit 1234, and the plurality of second gear units 1235*a* may be disposed to interlock with the plurality of first gear units 1234*a*.

The rotation sensor 1236 is a sensing device that may analyze the amount of rotation of the collimator 123, received from the second rotation transfer unit 1235, and sense the amount of rotation of the X-ray radiator 120. For example, the rotation sensor 1236 may be a position meter or an encoder. The rotation sensor 1236 may be disposed to be fixed to the inside of the collimator box 1230 by using a bracket 1238.

A rotation axis 1235*b* of the second rotation transfer unit 1235 may be fixed to one end of the rotation sensor 1236, and the second rotation transfer unit 1235 may be rotatably disposed to rotate on the rotation axis 1235*b*. Accordingly, the amount of rotation of the collimator 123, transferred by an interaction between the first rotation transfer unit 1234 and the second rotation transfer unit 1235, may be transferred to the rotation sensor 1236.

For example, when a user makes the collimator 123 rotate on the optical axis direction Z of X-rays to adjust an irradiation area of X-rays, the position of the connector 1237 disposed to be fixed to the X-ray source 122 is fixed, whereas the collimator 123 rotates on the optical axis direction Z of X-rays. In this case, the first rotation transfer unit 1234 disposed to be fixed to the connector 1237 and the second rotation transfer unit 1235 disposed to be fixed to the collimator 123 relatively rotate by using a pair of gear units 1234*a* and 1235*a*.

For example, when the collimator rotates on the optical axis direction Z of X-rays in a clockwise direction, the second rotation transfer unit 1235 and the rotation sensor 1236, disposed to be fixed to the collimator box 1230, also rotate on the optical axis direction Z of X-rays in the clockwise direction. In this case, the rotation axis 1235*b* of the second rotation transfer unit 1235 may be disposed to be fixed to the rotation sensor 1236, and the second gear units 1235*a* disposed along the outer circumferential surface of the second rotation transfer unit 1235 may rotate in a counterclockwise direction while interlocking with the first gear units 1234*a* of the first rotation transfer unit 1234, disposed to interact with the second gear units 1235*a*. Accordingly, the second rotation transfer unit 1235 may rotate on the rotation axis 1235*b* in the counterclockwise direction, and the rotation of the second rotation transfer unit 1235 may be transferred to the rotation sensor through the rotation axis 1235*b*. The rotation sensor 1236 may analyze a rotation transferred from the rotation axis 1235*b* of the second rotation transfer unit 1235 and thus sense the amount of rotation of the collimator 123 with respect to the X-ray source 122.

Figure 5:
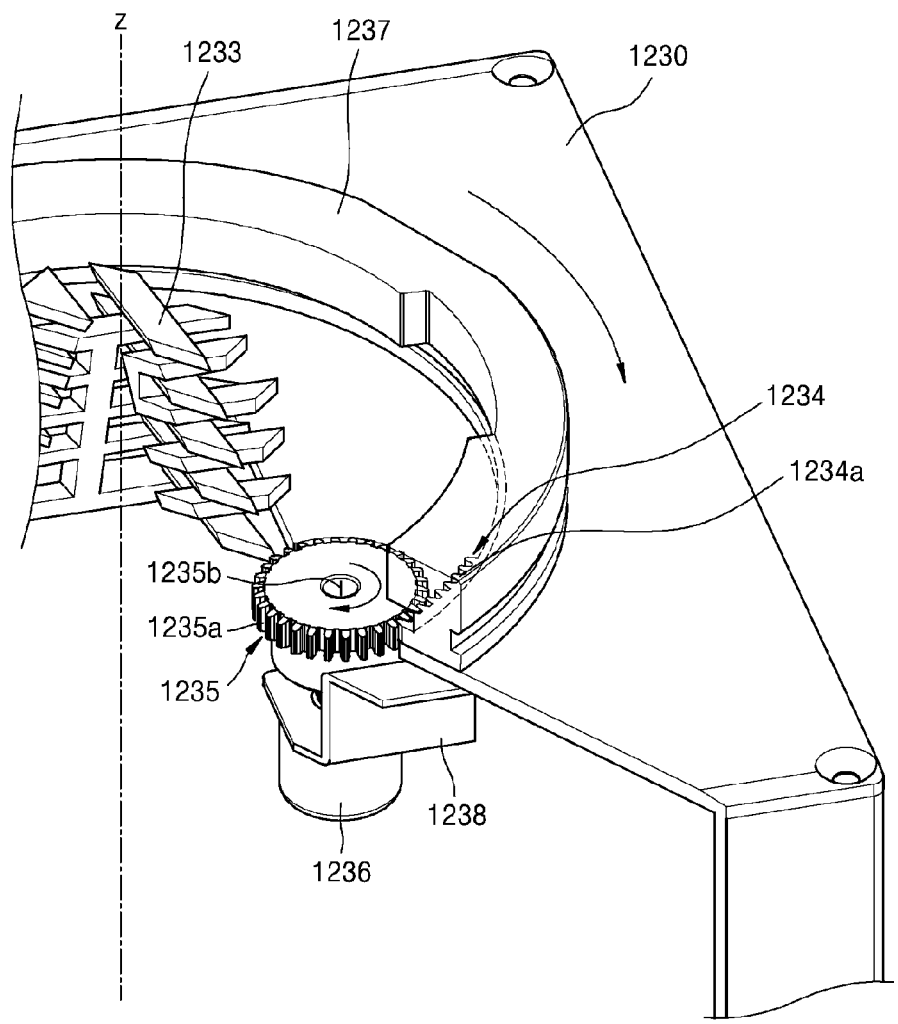
FIG. 5 is a sectional perspective view of a collimator including a connector according to another exemplary embodiment.

FIG. 5 is a perspective view of a collimator including a connector rotating on an optical axis direction Z of X-rays, according to another exemplary embodiment. Component elements that are the same as those of FIGS. 3A and 3B from among component elements illustrated in FIG. 5 use the same reference numerals as FIGS. 3A and 3B, and repeated descriptions are omitted.

Although the first rotation transfer unit 1234 and the second rotation transfer unit 1235 in FIGS. 3A and 3B are disposed outside the connector 1237, the embodiment concept is not limited thereto. Referring to FIG. 5, a rotation sensor 1236 and a second rotation transfer unit 1235 may be disposed inside a connector 1237. For example, a first rotation transfer unit 1234 formed in a ring shape may be disposed to be fixed along an inner circumferential surface of the connector 1237 formed in a ring shape. In this case, a plurality of first gear units 1234*a* may be disposed in an inner circumferential surface of the first rotation transfer unit 1234, and the rotation sensor 1236 may be disposed to be fixed to a collimator box 1230 by using a bracket 1238 in the inside of the connector 1237. The second rotation transfer unit 1235 formed in the shape of a disk may be disposed to rotate on a rotation axis 1235*b* fixed to one end of the rotation sensor 1236, and a plurality of second gear units 1235*a* may be disposed in an outer circumferential surface of the second rotation transfer unit 1235. The plurality of second gear units 1235*a* may rotate while interlocking with the plurality of first gear units 1234*a* of the first rotation transfer unit 1234.

As the collimator 123 rotates, the first gear units 1234*a* and the second gear units 1235*a* may rotate in the same direction while interlocking with each other. Thus, a rotation of the collimator 123 may be transferred to the rotation sensor 1236. A method of sensing the rotation of the collimator 123 by using the first rotation transfer unit 1234, the second rotation transfer unit 1235, and the rotation sensor 1236 is substantially the same as that described with reference to FIGS. 3A and 3B, and thus, a repeated description thereof is omitted.

Figure 6:
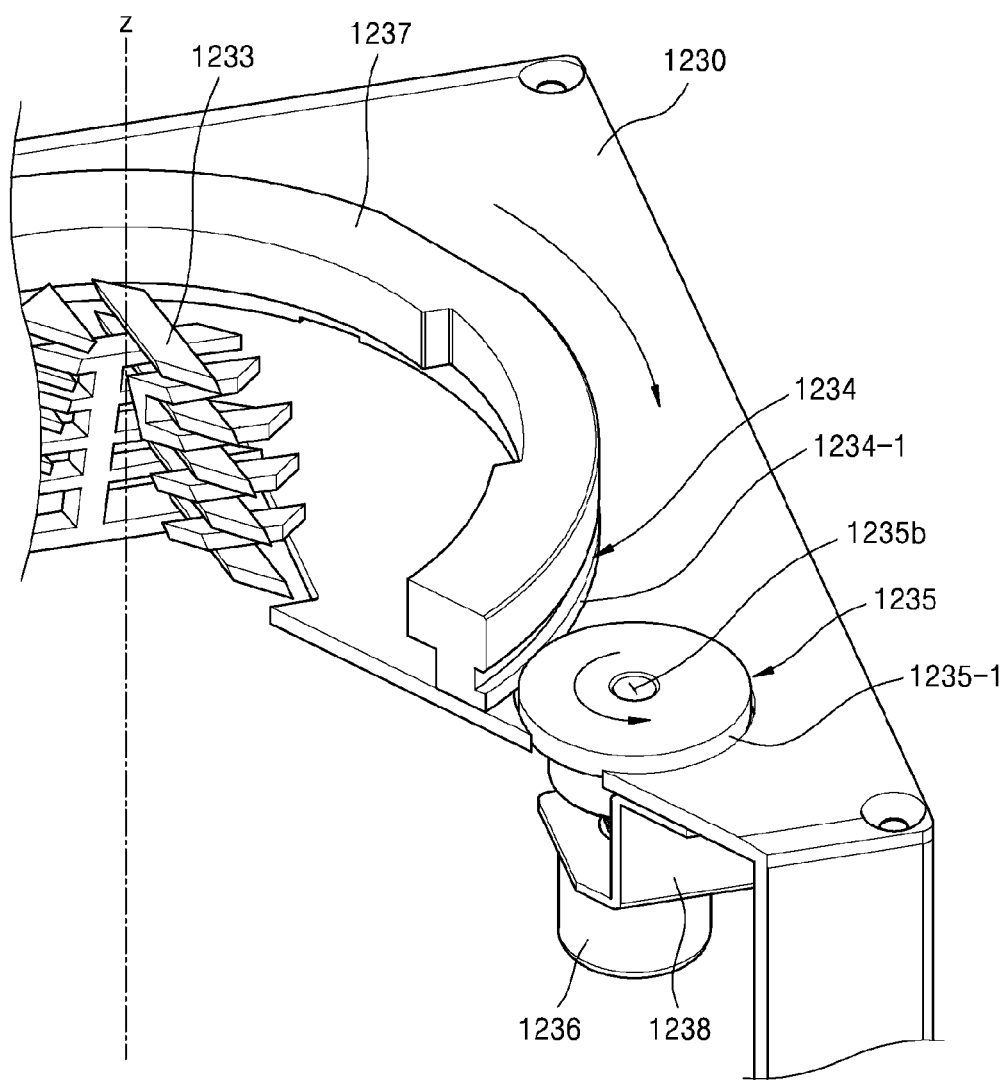
FIG. 6 is a sectional perspective view of a collimator including a connector according to another exemplary embodiment.
Figure 7:
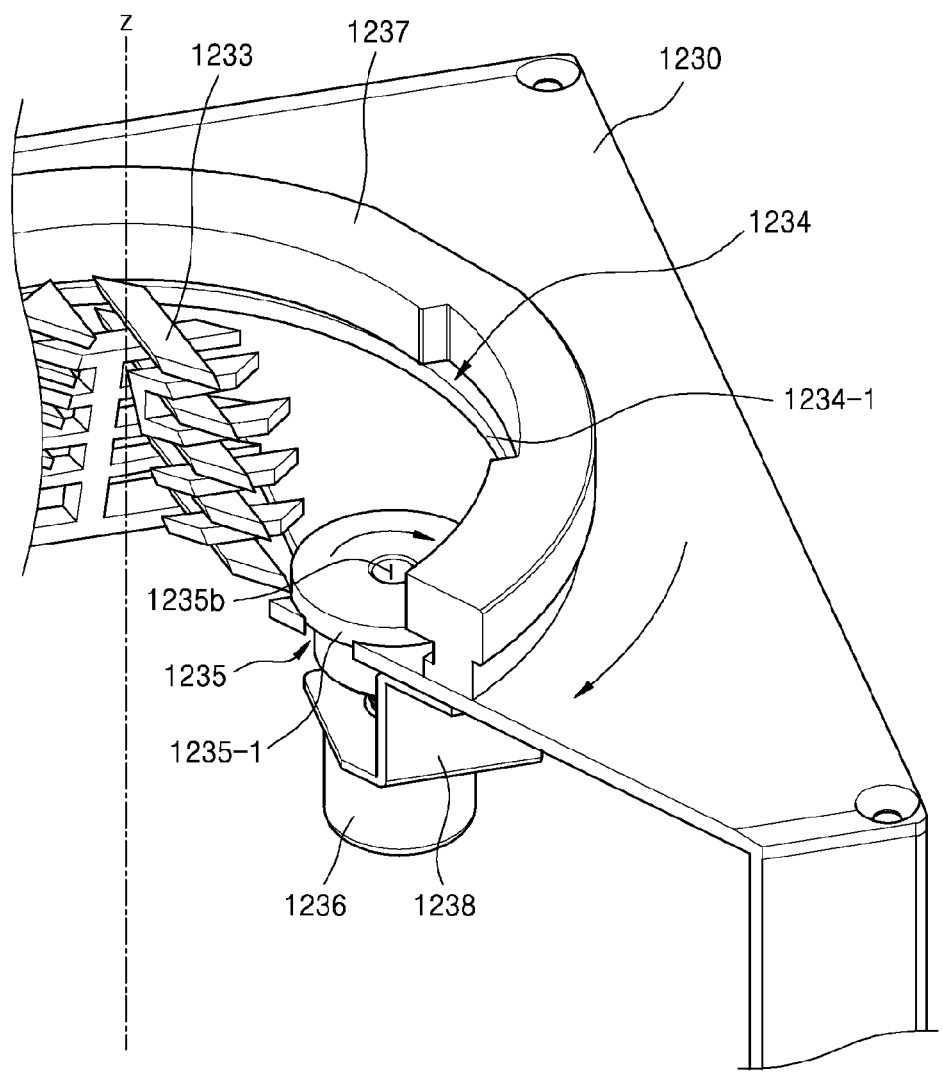
FIG. 7 is a sectional perspective view of a collimator including a connector according to another exemplary embodiment.

FIG. 6 is a perspective view of a collimator including a connector rotating on an optical axis direction Z of X-rays, according to another exemplary embodiment, and FIG. 7 is a perspective view of a collimator including a connector rotating on an optical axis direction Z of X-rays, according to another exemplary embodiment. Component elements that are the same as those of FIGS. 3A, 3B, and 5 from among component elements illustrated in FIGS. 6 and 7 use the same reference numerals as FIGS. 3A, 3B, and 5, and repeated descriptions are omitted.

Referring to FIG. 6, a first roller unit 1234-1 formed of a material having a high frictional force may be disposed along an outer circumferential surface of a ring-shaped first rotation transfer unit 1234 fixed to a connector 1237, and a second roller unit 1235-1 formed of a material having a high frictional force may be disposed along an outer circumferential surface of a second rotation transfer unit 1235 so as to contact the first roller unit 1234-1 of the first rotation transfer unit 1234 and move in a sliding manner. In this case, a rotation sensor 1236 and the second rotation transfer unit 1235 may be disposed outside the connector 1237.

Referring to FIG. 7, a first roller unit 1234-1 formed of a material having a high frictional force may be disposed along an inner circumferential surface of a ring-shaped first rotation transfer unit 1234 fixed to a connector 1237, and a second roller unit 1235-1 formed of a material having a high frictional force may be disposed along an outer circumferential surface of a second rotation transfer unit 1235 so as to contact the first roller unit 1234-1 of the first rotation transfer unit 1234 and slidingly move. In this case, a rotation sensor 1236 and the second rotation transfer unit 1235 may be disposed inside the connector 1237.

Referring to FIGS. 6 and 7, as the collimator 123 rotates, the first roller unit 1234-1 of the first rotation transfer unit 1234 and the second roller unit 1235-1 of the second rotation transfer unit 1235 may rotate while contacting each other. Thus, a rotation of the collimator 123 may be transferred to the rotation sensor 1236. A method of sensing the rotation of the collimator 123 by using the first rotation transfer unit 1234, the second rotation transfer unit 1235, and the rotation sensor 1236 is substantially the same as that described with reference to FIGS. 3A and 3B, and thus, a repeated description thereof is omitted.

In FIGS. 5 and 6, although a pair of gear units (i.e., the first and second gear units 1234a and 1235a) or a pair of roller units (i.e., the first and second roller units 1234-1 and 1235-1) are disposed so that the first rotation transfer unit 1234 and the second rotation transfer unit 1235 may interlock with each other and transfer a rotation, the embodiment concept is not limited thereto. For example, the first rotation transfer unit 1234 and the second rotation transfer unit 1235 may include any structure in which the first rotation transfer unit 1234 and the second rotation transfer unit 1235 may interact with each other to transfer a rotation. In addition, also in a case in which the first rotation transfer unit 1234 and the second rotation transfer unit 1235 are separate from each other, as well as in a case in which they contact each other, a rotation transfer unit, such as a chain or a belt, may be additionally disposed so that the first rotation transfer unit 1234 and the second rotation transfer unit 1235 may transfer their rotation to each other.

Figure 8:
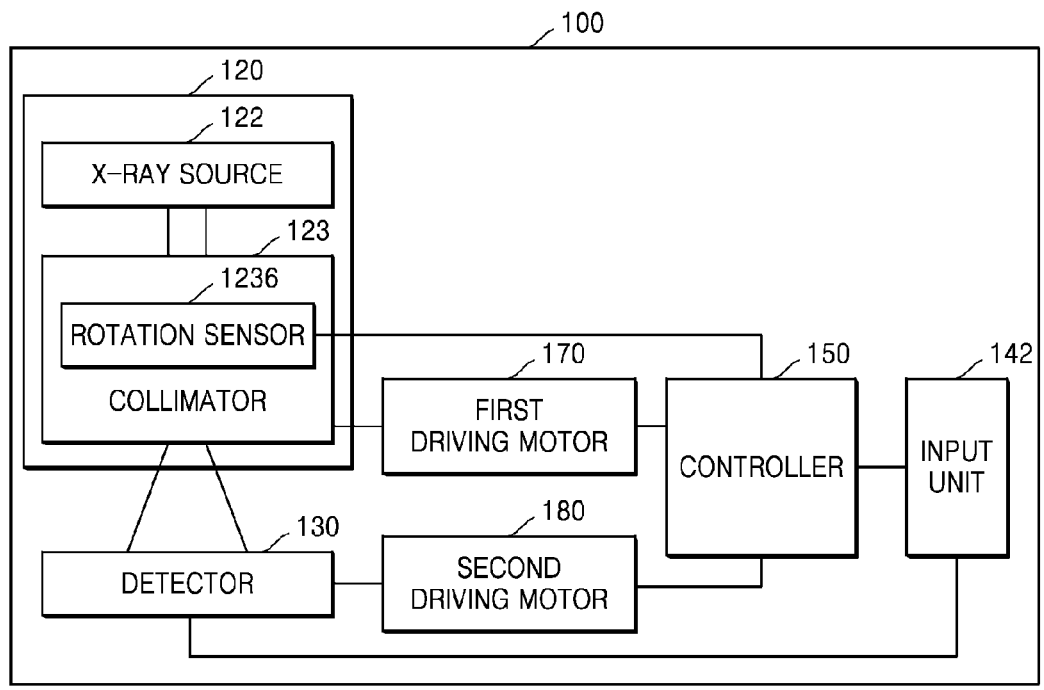
FIG. 8 is a block diagram of an X-ray apparatus according to an exemplary embodiment.
Figure 9A:
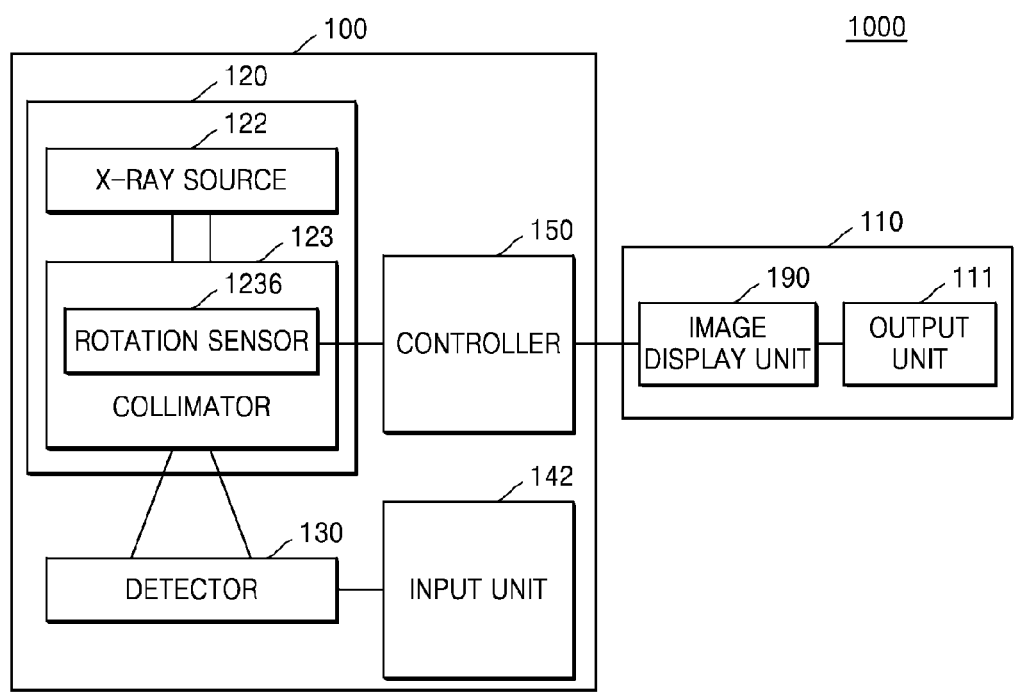
FIG. 9A is a block diagram of an X-ray system according to another exemplary embodiment.
Figure 9B:
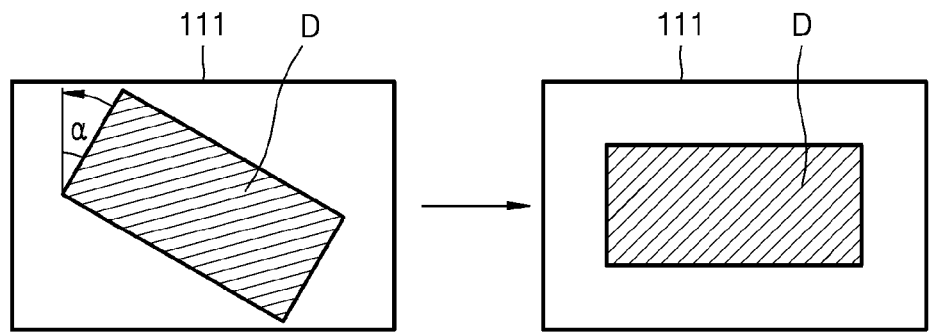
FIG. 9B is a front view of an output unit aligned according to the X-ray system illustrated in FIG. 9A.

FIG. 8 is a block diagram of an X-ray apparatus 100 according to an exemplary embodiment. FIG. 9A is a block diagram of an X-ray system 1000 according to another exemplary embodiment, and FIG. 9B is a front view of an output unit aligned according to the X-ray system 1000 illustrated in FIG. 9A.

As illustrated in FIGS. 4A and 4B, as a user rotates a collimator 123 to adjust an irradiation area of an object, a radiation field A of X-rays and a receiving surface 131 of a detector 130 may be misaligned. To align the radiation field A of X-rays with the receiving surface 131 of the detector 130, the collimator 123 or the detector 130 may be rotated by using the amount (e.g., a first angle α) of rotation of the collimator 123, sensed by a rotation sensor 1236.

Referring to FIGS. 4A, 4B, and 8, the rotation sensor 1236 may transfer the sensed amount of rotation of the collimator 123 to a controller 150. The controller 150 may compare the amount of rotation of the collimator 123 to the position of the detector 130 input beforehand through an input unit 142 to calculate the extent of misalignment between the radiation field A of X-rays and the receiving surface 131 of the detector 130, and may convert the calculated extent of misalignment into a control signal and transmit the control signal to a plurality of driving motors.

For example, when a fixed-type detector whose position is fixed is used as the detector 130, the X-ray apparatus 100 may further include a first driving motor 170 that may rotate the collimator 123 about the optical axis direction Z of X-rays. The first driving motor 170 may adjust the alignment between the radiation field A of X-rays and the receiving surface 131 of the detector 130 by receiving a driving signal from the controller 150 and making the collimator 123 rotate on the optical axis direction Z of X-rays in a counterclockwise direction by the first angle α.

As another example, when a mobile detector is used as the detector 130, the X-ray apparatus 100 may further include a second driving motor 180 that may make the detector 130 rotate on the optical axis direction Z of X-rays. The second driving motor 180 may adjust the alignment between the radiation field A of X-rays and the receiving surface 131 of the detector 130 by receiving a driving signal from the controller 150 and making the detector 130 rotate on the optical axis direction Z of X-rays in a clockwise direction by the first angle α. However, the embodiment concept is not limited thereto. For example, the controller 150, which receives the amount of rotation of the collimator 123 from the rotation sensor 1236, may adjust the alignment between the radiation field A of X-rays and the receiving surface 131 of the detector 130 by applying a driving signal to the first driving motor 170 and the second driving motor 180 and making the controller 150 and the detector 130 simultaneously rotate on the optical axis direction Z of X-rays.

As illustrated in FIGS. 4A and 4B, when the radiation field A of X-rays and the receiving surface 131 of the detector 130 are misaligned as a user rotates the collimator 123 to adjust an irradiation area of an object, a portion of an image output to the output unit 111 may be cut or may be expressed to be unsuitable for a desired size. To make up for such a problem, the image may be corrected by using an Auto-Corp method and a corrected image may be output. In this case, if the amount of rotation of the collimator 123 may be sensed, the image may be more easily corrected since the amount of rotation of the image may be easily sensed.

Referring to FIGS. 4A, 4B, and 9, the rotation sensor 1236 may transfer the sensed amount of rotation of the collimator 123 to the controller 150. The controller 150 may compare the amount of rotation of the collimator 123 to the position of the detector 130 input beforehand through an input unit 142 to calculate the extent of misalignment between the radiation field A of X-rays and the receiving surface 131 of the detector 130, and an image display unit 190 may convert the calculated extent of misalignment into an image signal and transmit the image signal to an output unit 111.

For example, referring to FIG. 9B, when the radiation field A of X-rays and the receiving surface 131 of the detector 130 are misaligned clockwise by the first angle α due to the rotation of the collimator 123, the rotation sensor 1236 may transmit the amount of rotation of the collimator 123 to the controller 150. The controller 150 may transmit a detection signal received from the detector 130 and a position signal received from the rotation sensor 1236 to the image display unit 190, and the image display unit 190 may calculate the amount of rotation of an image depending on the received position signal and transmit an image signal, rotated in a counterclockwise direction by the first angle α, to the output unit 111. Accordingly, the output unit 111 may output an aligned image D.

Figure 10:
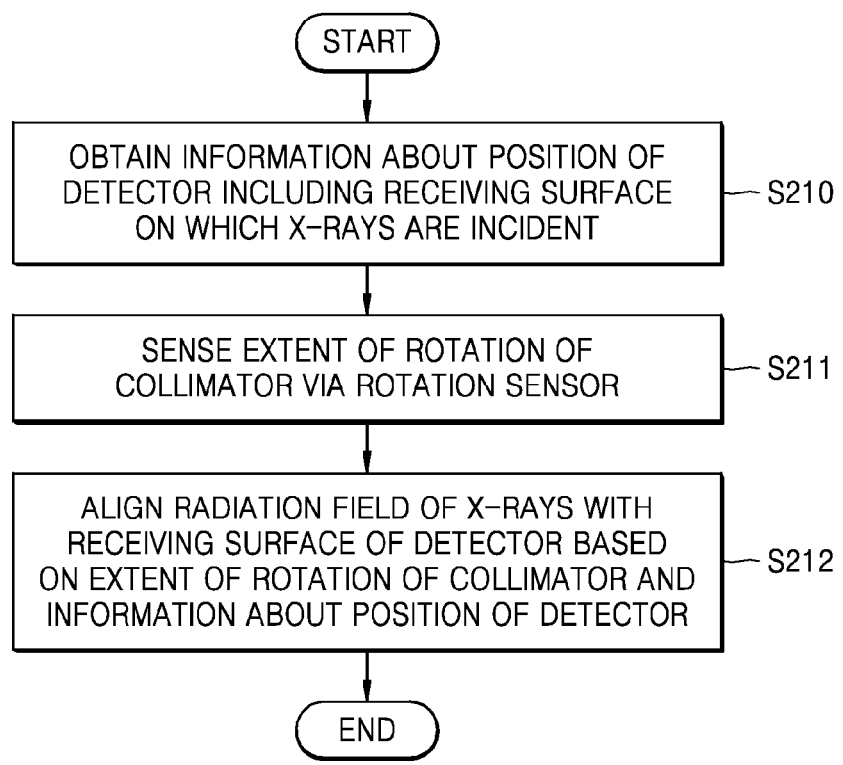
FIG. 10 is a flowchart of a method of operating an X-ray apparatus, according to an exemplary embodiment.

FIG. 10 is a flowchart illustrating a method of operating the X-ray apparatus 100, according to an exemplary embodiment.

The X-ray apparatus 100 may obtain information about the position of the detector 130 including the receiving surface 131 on which X-rays are incident (operation S210). For example, when the detector 130 of the X-ray apparatus 100 is a fixed-type detector, the information about the position of the detector 130 may be stored in a memory (not shown). When the detector 130 of the X-ray apparatus 100 is a mobile detector, the controller 150 of the X-ray apparatus 100 may obtain information about the position of the detector 130 as a user inputs the information about the position of the detector 130 by using the input unit 112.

When the collimator 123 is rotated to adjust an irradiation area of X-rays radiated to an object, the amount of rotation of the collimator 123 may be sensed by using the rotation sensor 1236 (operation S211). As described above, the first rotation transfer unit 1234 and the second rotation transfer unit 1235 may be disposed to be fixed to the X-ray source 122 and the collimator 123, respectively, to sense the amount of rotation of the collimator 123, and the amount of rotation of the collimator 123 may be sensed by using a rotation transmitted to the rotation sensor 1236 by an interaction between the first rotation transfer unit 1234 and the second rotation transfer unit 1235.

When the amount of rotation of the collimator 123 is sensed, the radiation field A of X-rays and the receiving surface 131 of the detector 130 may be aligned by using the information about the position of the detector 130 (operation S212).

For example, when the detector 130 of the X-ray apparatus 100 is a fixed-type detector, the radiation field A of X-rays and an active region of the detector 130 may be aligned by rotating the collimator 123 by using the first driving motor 170 that may drive the collimator 123.

When the detector 130 of the X-ray apparatus 100 is a mobile detector, the radiation field A of X-rays and the receiving surface 131 of the detector 130 may be aligned by rotating the detector 130 by using the second driving motor 180 that may drive the detector 130. In this case, the collimator 123 and the detector 130 may be simultaneously rotated by simultaneously driving the first driving motor 170 and the second driving motor 180 to align the radiation field A of X-rays and the receiving surface 131 of the detector 130.

Figure 11:
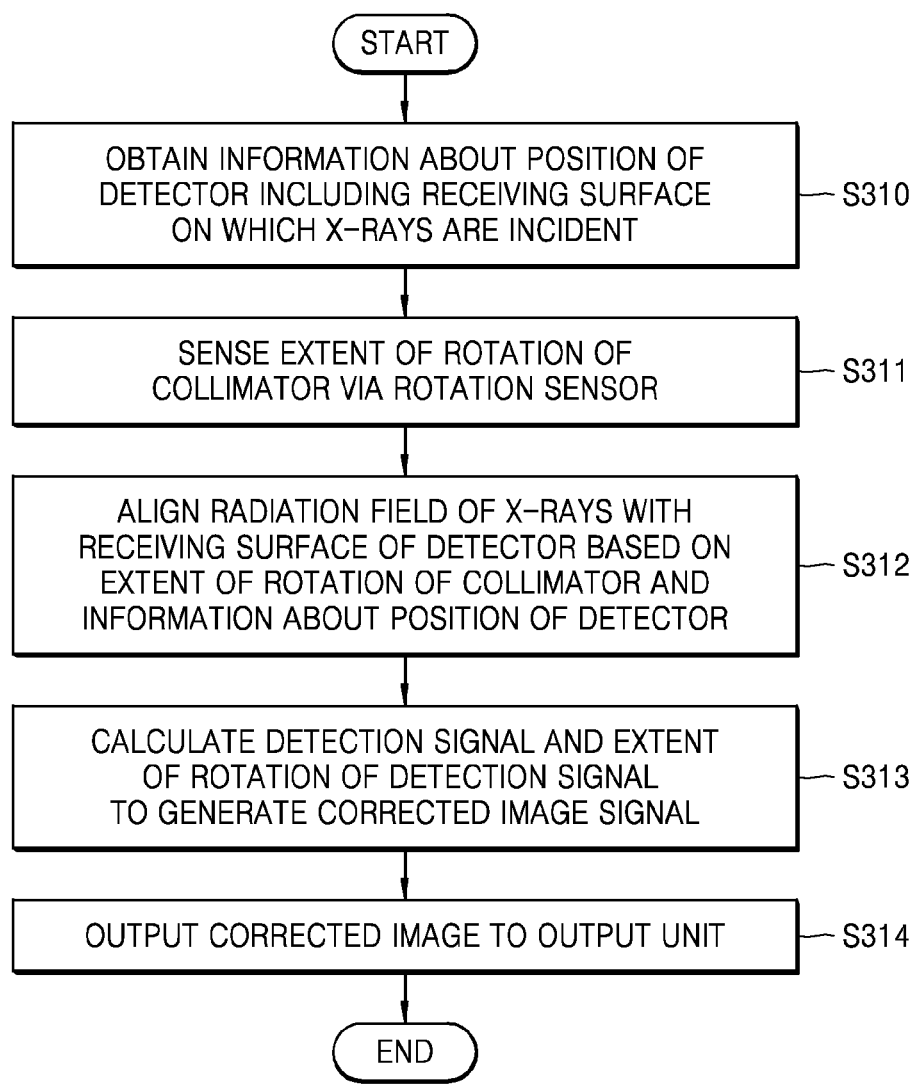
FIG. 11 is a flowchart of a method of operating an X-ray apparatus, according to another exemplary embodiment.

FIG. 11 is a flowchart of a method of operating the X-ray apparatus 100, according to another exemplary embodiment.

The X-ray apparatus 100 may obtain information about the position of the detector 130 including the receiving surface 131 on which X-rays are incident (operation S310). When the collimator 123 is rotated to adjust an irradiation area of X-rays radiated to an object, the amount of rotation of the collimator 123 may be sensed by using the rotation sensor 1236 (operation S311).

The operation S310 of obtaining the information about the position of the detector 130 and the operation S311 of sensing the amount of rotation of the collimator 123 are substantially the same as the operation S210 and the operation S211, respectively, described with reference to FIG. 10, and thus, repeated descriptions are omitted.

The amount of rotation of a detection signal generated by the receiving surface 131 of the detector 130 may be determined by using the amount of rotation of the collimator 123 and a detection signal sensed by the detector 130 (operation S312).

For example, when the radiation field A of X-rays and the receiving surface 131 of the detector 130 are misaligned by a predetermined angle due to the rotation of the collimator 123, the rotation sensor 1236 may transmit the amount of rotation of the collimator 123 to the controller 150. The controller 150 may transmit the amount of rotation of the detection signal, generated by the receiving surface 131 of the detector 130, to the image display unit 190 by using the detection signal received from the detector 130 and the position signal received from the rotation sensor 1236.

The image display unit 190 may calculate the received detection signal and the amount of rotation of the detection signal to generate a corrected image signal (operation S313).

The embodiments can be implemented in computing hardware (computing apparatus) and/or software, such as (in a non-limiting example) any computer that can store, retrieve, process and/or output data and/or communicate with other computers. The results produced can be displayed on a display of the computing hardware. A program/software implementing the embodiments may be recorded on computer-readable media comprising computer-readable recording media. The program/software implementing the embodiments may also be transmitted over transmission communication media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW. An example of communication media includes a carrier-wave signal.

Further, according to an aspect of the embodiments, any combinations of the described features, functions and/or operations can be provided.

The output unit 111 may output a corrected image by using the image signal received from the image display unit 190 (operation S314).

The exemplary embodiments of the embodiment concept can be written as computer programs and can be implemented in general-use digital computers that execute the programs using a computer readable recording medium.

Examples of the computer readable recording medium include magnetic storage media (e.g., ROM, floppy disks, hard disks, etc.), optical recording media (e.g., CD-ROMs, or DVDs), etc.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An X-ray apparatus, comprising:
an X-ray source to radiate X-rays;
a collimator which is rotatable on an optical axis direction of the X-rays to adjust a radiation field of the X-rays;
a ring-shaped first rotation transfer device on the X-ray source;
a second rotation transfer device on the collimator so as to rotate with rotation of the collimator, the second rotation transfer device being engaged with the ring-shaped first rotation transfer device so as to rotate around the ring-shaped first rotation transfer device as the collimator rotates;
a rotation sensor which, based on an amount of rotation of the second rotation transfer device, senses an amount of rotation of the collimator with respect to the X-ray source;
a detector having a receiving surface on which the X-rays radiated from the X-ray source and having the radiation field adjusted by the collimator are incident;
a processor which calculates, based on the amount of rotation of the collimator sensed by the rotation sensor, a misalignment between the radiation field adjusted by the collimator and the receiving surface; and
an output unit which outputs an X-ray image in which the calculated misalignment is corrected.

2. The X-ray apparatus of claim 1, further comprising:
an image generator configured to generate an image signal based on a detection signal generated by the X-rays incident on the receiving surface of the detector and the amount of rotation sensed by the rotation sensor.

3. An X-ray apparatus, comprising:
an X-ray source to radiate X-rays;
a collimator to adjust a radiation field of the X-rays radiated by the X-ray source;
a connector having a ring shape with open ends, with one end of the connector fixed to the X-ray source and an other end of the connector rotatably connected to the collimator, so that the collimator is rotatable with respect to the X-ray source on an optical axis direction of the X-rays;
a ring-shaped first rotation transfer device on the X-ray source;
a second rotation transfer device on the collimator so as to rotate with rotation of the collimator, the second rotation transfer device being engaged with the ring-shaped first rotation transfer device so as to rotate around the ring-shaped first rotation transfer device as the collimator rotates;
a rotation sensor to sense an amount of rotation of the second rotation transfer device; and
a detector having a receiving surface on which the X-rays radiated from the X-ray source and having the radiation field adjusted by the collimator are incident.

4. The X-ray apparatus of claim 3, wherein the ring-shaped first rotation transfer device is positioned along an outer circumferential surface of the connector, and the second rotation transfer device and the rotation sensor are positioned outside the connector.

5. The X-ray apparatus of claim 4, wherein the ring-shaped first rotation transfer device and the second rotation transfer device commonly comprise a pair of gears that rotate while being interlocked with each other.

6. The X-ray apparatus of claim 4, wherein the ring-shaped first rotation transfer device and the second rotation transfer device commonly comprise a pair of roller devices that rotate according to a sliding motion while being in contact with each other.

7. The X-ray apparatus of claim 3, wherein the ring-shaped first rotation transfer device is positioned along an inner circumferential surface of the connector, and the second rotation transfer device and the rotation sensor are positioned inside the connector.

8. The X-ray apparatus of claim 7, wherein the ring-shaped first rotation transfer device and the second rotation transfer device commonly comprise a pair of gears that rotate while being interlocked with each other.

9. The X-ray apparatus of claim 7, wherein the ring-shaped first rotation transfer device and the second rotation transfer device commonly comprise a pair of roller devices that rotate according to a sliding motion while being in contact with each other.

10. The X-ray apparatus of claim 3, wherein the collimator further comprises: an X-ray entrance window through which the X-rays enter and an X-ray exit window through which the X-rays exit; and a radiation field range adjustor disposed in the X-ray entrance window and the X-ray exit window.

11. A method of operating an X-ray apparatus that includes an X-ray source to radiate X-rays, a collimator which is rotatable on an optical axis direction of the X-rays to adjust a radiation field of the X-rays, and a detector having a receiving surface on which the X-rays radiated from the X-ray source and having the radiation field adjusted by the collimator are incident, the method comprising:
obtaining information about a position of the detector;
sensing, via a rotation sensor, an amount of rotation of the collimator;
determining an amount of rotation of a detection signal generated by the X-rays incident on the receiving surface of the detector, based on the sensed amount of rotation of the collimator and the obtained information about the position of the detector;
generating a corrected image signal based on the determined amount of rotation of the detection signal; and
outputting an image in accordance with the corrected image signal.

* * * * *